United States Patent
Patil et al.

(10) Patent No.: US 10,687,723 B2
(45) Date of Patent: Jun. 23, 2020

(54) METHOD AND A SYSTEM FOR AUTOMATIC LABELING OF ACTIVITY ON ECG DATA

(71) Applicant: KONINKLIJKE PHILIPS N.V., Eindhoven (NL)

(72) Inventors: Ravindra Balasaheb Patil, Bangalore (IN); Rajendra Singh Sisodia, Bhopal (IN); Krishnamoorthy Palanisamy, Bangalore (IN); Nagaraju Bussa, Bangalore (IN); Vikram Basawaraj Patil Okaly, Bangalore (IN); Larry Nielsen, Burlington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 142 days.

(21) Appl. No.: 15/744,918

(22) PCT Filed: Jul. 12, 2016

(86) PCT No.: PCT/EP2016/066459
§ 371 (c)(1),
(2) Date: Jan. 15, 2018

(87) PCT Pub. No.: WO2017/012906
PCT Pub. Date: Jan. 26, 2017

(65) Prior Publication Data
US 2018/0206751 A1    Jul. 26, 2018

(30) Foreign Application Priority Data
Jul. 21, 2015 (EP) .................................... 15177683

(51) Int. Cl.
*A61B 5/0452* (2006.01)
*A61B 5/04* (2006.01)
(Continued)

(52) U.S. Cl.
CPC ........ *A61B 5/04017* (2013.01); *A61B 5/0452* (2013.01); *A61B 5/0816* (2013.01);
(Continued)

(58) Field of Classification Search
CPC ........................... A61B 5/1118; A61B 5/0452
See application file for complete search history.

(56) References Cited

U.S. PATENT DOCUMENTS

| | | | |
|---|---|---|---|
| 5,836,987 | A | 11/1998 | Baumann |
| 7,167,743 | B2 | 1/2007 | Heruth |

(Continued)

FOREIGN PATENT DOCUMENTS

| | | |
|---|---|---|
| EP | 2845539 | 3/2015 |
| WO | 2014/053538 | 4/2014 |

OTHER PUBLICATIONS

Altini et al; "Combining wearable accelercmeter and physiological data for activity and energy expenditure estimation", Proceedings of the 4th Conference on Wireless Health, WH '13, Jan. 1, 2013.
(Continued)

*Primary Examiner* — George R Evanisko

(57) ABSTRACT

The present invention relates to a method of automatic labeling of activity of a subject on ECG data. The method of the invention comprises acquiring at least one physiological input signal purporting to an ECG signal and processing thereof. The processing of the at least one physiological input signal comprises conditioning the ECG signal and processing thereof, wherein the processing comprises obtaining respiration data from the ECG signal, identifying the activity pertaining to the said ECG data based on at least a signal specific feature of the said ECG signal, wherein the respiration data are used for differentiating activities performed by the subject, and labeling the said ECG data with the said activity, automatically. The present invention also
(Continued)

relates to a system for automatic labeling of activity on ECG data in accordance with the method of the invention.

9 Claims, 5 Drawing Sheets

(51) Int. Cl.
*A61B 5/00* (2006.01)
*A61B 5/08* (2006.01)
*A61B 5/11* (2006.01)
*A61B 5/0205* (2006.01)

(52) U.S. Cl.
CPC .......... *A61B 5/1118* (2013.01); *A61B 5/7264* (2013.01); *A61B 5/0205* (2013.01); *A61B 5/04014* (2013.01); *A61B 5/7278* (2013.01)

(56) References Cited

U.S. PATENT DOCUMENTS

| | | | |
|---|---|---|---|
| 2007/0032733 A1* | 2/2007 | Burton | A61B 5/02405 600/509 |
| 2008/0300641 A1 | 12/2008 | Brunekreeft | |
| 2011/0245688 A1 | 10/2011 | Arora | |
| 2014/0330146 A1 | 11/2014 | Kuppuraj | |

OTHER PUBLICATIONS

Smolander et al: "A new heart rate variability-based method for the estimation of oxygen consumption without individual laboratoryke calibration: Application example on postal workers". Applied Ergonomics, Butterworth Scientific Ltd, Guildford, GB, vol . 39, No. 3, Oct. 24, 2007.

Pawar et al: "Body Movement Activity Recognition for Ambulatory Cardiac Monitoring", IEEE Transactions on Biomedical Engineering, IEEE Service Center, Piscataway, NJ, USA, vol. 54 , No. 5, May 1, 2007.

Kher et al: "Physical activities recognition from ambulatory ECG signals using neuro-fuzzy classifiers and support vector machines", Journal of Medical Engineering & Technology, vol. 39, No. 2, Feb. 28, 2015.

Li et al: "Multimodal Physical Activity Recognition by Fusing Temporal and Cepstral Information", IEEE Transactions on Neural Systems and Rehabilitationengineering, IEEE Service Center, New York, NY, US, vol. 18 , No. 4, Aug. 1, 2010.

Moody G B: "ECG-based indices of physical activity", Computers in Cardiology 1992, Proceedings of Durham, NC, USA Oct. 11-14, 1992, Los Alamitos, CA, USA,IEEE Comput. Soc, US, Oct. 11, 1992.

Sriram et al: "Activity-aware ECG-based patient authentication for remote health monitoring", Proceedings of the 2009 International Conference on Multimodal Interfaces, ICMI-MLMI '09, Jan. 1, 2009.

Garcia et al: "ECG-based detection of body position changes in ischemia monitoring", IEEE Transactions on Biomedical Engineering, IEEE Service Center, PI Scataway, NJ, USA, vol. 50, No. 6, Jun. 1, 2003.

* cited by examiner

METHOD AND A SYSTEM FOR AUTOMATIC LABELING OF ACTIVITY ON ECG DATA

CROSS REFERENCE TO RELATED APPLICATIONS

This application is the U.S. National Phase application under 35 U.S.C. § 371 of International Application No. PCT/EP2016/066459, filed Jul. 12, 2016, published as WO 2017/012906 on Jan. 26, 2017, which claims the benefit of European Patent Application Number 15177683.8 filed Jul. 21, 2015. These applications are hereby incorporated by reference herein.

FIELD OF THE INVENTION

The invention relates to Electrocardiography (ECG) data. More particularly, to auto labeling of activity on ECG data indicating the activity performed by the subject while obtaining the ECG.

BACKGROUND

The rising average life expectancy and higher ratio of seniors in the population increased the prevalence of chronic diseases. Long term medical care is required for larger proportion of such subjects, besides decreasing the length of stay in hospitals. Preventive health care providing patient monitoring at home or residence, reducing the readmission rates at the hospital, has been a major motivational factor for personal health monitoring in line with patient monitoring.

Mobile medical sensors provide an efficient, accurate and economical means to monitor the health of the subject outside the hospital. There has been a tremendous increase in the number of wearable devices employing mobile medical sensors to monitor the health of the subject, and has gained importance in personal health care monitoring and its system.

Currently, the wearable device have the capability to collect single lead ECG signal and continuously store the data and upload the same into the cloud for further analysis. It becomes very useful to identify the state or condition of the subject at the time of obtaining the ECG. In other words, identifying the activity that been performed by the subject while obtaining ECG provides a greater insight into the understanding and analyzing the ECG data.

ECG data along with the activity information becomes very helpful in providing proper diagnosis to the subject, wherein such diagnosis relies upon the ECG data. Accordingly, current technology employs accelerometer to detect the activity of the subject when the ECG is being obtained. The activity information is stored along with the ECG. Since the ECG data and the activity information using the accelerometer are obtained independent of each other, mapping of these two data/information is required. Also, not all the activities of the subject can be detected correctly. The accelerometer detects and measures only the motion and not exertion no matter how hard the subject is straining or the deadlift is. For instance, the motion detected by the accelerometer from eating seems more vigorous than the bicep curls. Also, the activities such as sleep, rest or sitting idle cannot be differentiated properly. Due to this set back, mapping the activity with the ECG data is not robust and has reduced reliability.

US20110245688 A1 requires ECG signal along with a motion detection feature to identify the activity of the person. Here, ECG and a plurality of sensors are communicatively coupled along with motion detection feature. Real time synchronization of ECG data and motion data needs to be dealt with carefully.

US20080300641A1 deals with generating cardiac information descriptive of cardiac functioning of a patient, detecting a cardiac anomaly based on an analysis of the cardiac information. It also discloses generating activity information descriptive of physical activity of the patient during the cardiac anomaly, and associating the cardiac information and the activity information, during the cardiac anomaly.

It is well appreciated that the ECG do provide a lot of information regarding the health of the subject. However, for more accurate diagnosis the activity being performed by the subject when the ECG was recorded need to be known along with the ECG. The invention is aimed at overcoming the problems associated with mapping of the ECG data and the activity information obtained independently. The invention proposes to auto label the ECG data with the activity information by deciphering only the ECG signal.

OBJECTS OF THE INVENTION

It is an object of the invention to provide a method for automatically labeling the activity been performed while obtaining ECG, in the ECG data.

It is another object of the invention to provide the information on the activity been performed from the ECG signal.

It is further object of the invention to provide activity information along with the ECG data to enable further diagnosis more accurate and appropriate.

It is yet another object of the invention to provide a system for performing the method of the invention for automatically labeling the activity been performed while obtaining ECG, in the ECG data.

SUMMARY OF THE INVENTION

The invention provides a method for automatic labeling of activity of a subject on electrocardiography (ECG) data. The method of the invention comprises of acquiring at least one physiological input signal relating to an ECG signal, and processing of the physiological input signal. The processing of the physiological input signal comprises of conditioning the ECG signal, obtaining respiration data from the said ECG signal. The respiration data is deciphered from the ECG signal. The method comprises identifying the activity pertaining to the said ECG data based on at least a signal specific feature of the said ECG signal, and labeling the said ECG data with the said activity, automatically.

The processing of the ECG signal comprises identifying the fiducial points in at least one of the segment of the ECG signal. Performing fragment analysis on the said segment of the ECG signal, fitting the ST and PQ segments of the ECG signal based on cubic spline fitting to provide fitted segment of the ECG signal. The fragment analysis preferentially refers to extracting pertinent information from the respective segment, especially from ST and PQ segments, like eigen values of principal components obtained by applying Karhunen Loeve Transform (KLT) on the respective segment.

Thus, in an embodiment identifying the activity comprises applying KLT on the fitted segment of the ECG signal to obtain principal component values, computing the eigen values of the said principal components to obtain the feature set, and classifying the said feature set based on the classifier model to map the feature set to its corresponding activity.

The classifier model can be based on at least one of the said physiological inputs and has information pertaining to different activities. In an embodiment the classifier uses the eigen values and the respiration rate as the feature set.

The invention also provides a system for auto labeling activity of a subject on ECG data in accordance with the method of the invention. The system comprises an acquisition unit for acquiring at least one physiological input purporting to an ECG signal, a processing unit for processing the at least one physiological input. The processing unit comprises a conditioning unit for conditioning the ECG signal, wherein the processing comprises obtaining respiration data from the ECG signal, and an identification unit for identifying the activity pertaining to the said ECG data based on a signal specific feature of the ECG signal, wherein the respiration data are used for differentiating activities performed by the subject.

In an embodiment the conditioning unit comprises of adaptive band pass filter. Moreover, in an embodiment the processing unit is provided for identifying the fiducial points in at least one of the segment of the ECG signal. The processing unit can be provided for performing fragment analysis on the segment of the ECG signal. In an embodiment the processing unit is provided for fitting the ST and PQ segments of the ECG signal based on cubic spline fitting to provide fitted segment of the ECG signal. Furthermore, in an embodiment the identification unit is provided for applying KLT on the fitted segment of the ECG signal to obtain principal component values. In particular, the identification unit is provided for computing the eigen values of the principal components to obtain the feature set. In an embodiment the identification unit is provided for classifying the feature set based on the classifier model to map the feature set to its corresponding activity. The classifier model can be based on at least one of the physiological inputs.

BRIEF DESCRIPTION OF THE DRAWINGS

With reference to the accompanying drawings in which.

DETAILED DESCRIPTION

The invention is hereinafter described with reference to non-exhaustive exemplary embodiment and with reference to FIGS. 1 to 5.

As herein before referred, the invention propose to automatically identify and label the ECG data with the activity being performed by the subject while obtaining the ECG. The automatic labeling of activity on the ECG data enables to provide diagnosis to the subject more appropriately.

Figure 1:
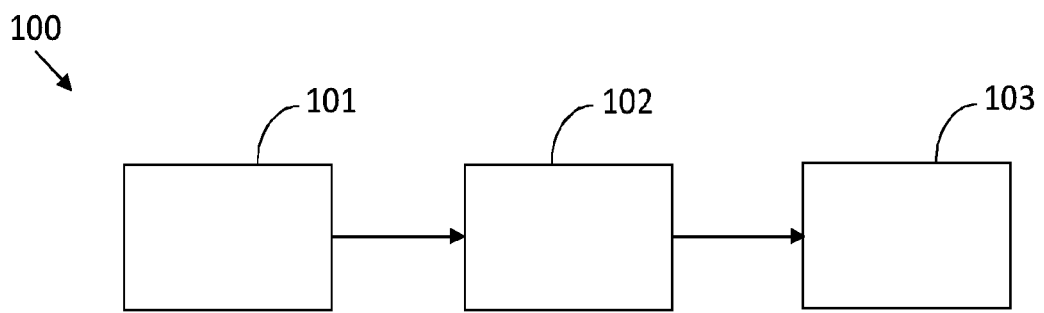
FIG. 1 shows the system for automatic labeling of activity on the ECG data, in accordance with the invention.
Figure 2:
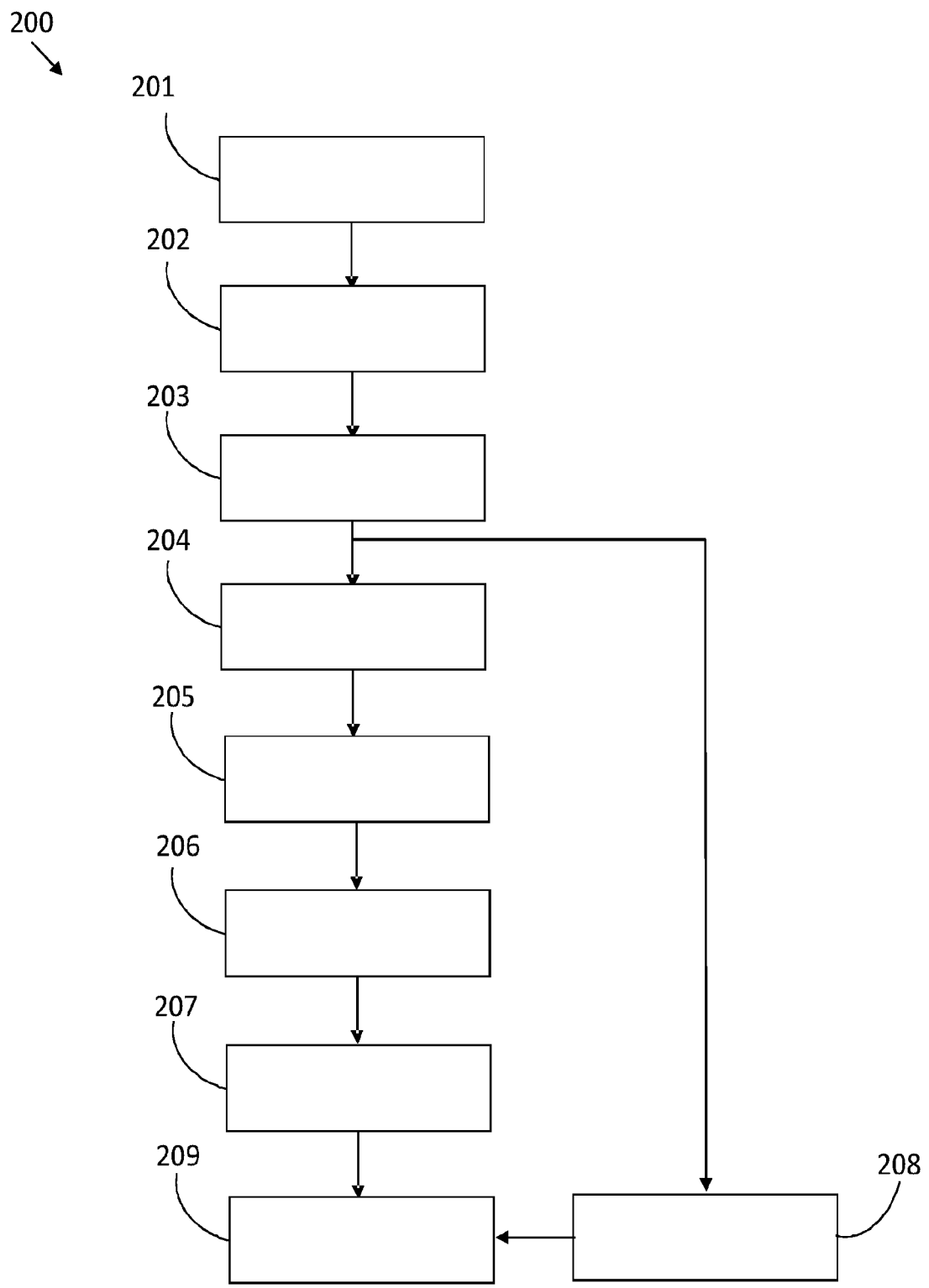
FIG. 2 shows the method for automatic labeling of activity on the ECG data, in accordance with the invention.

FIGS. 1 and 2 shows a system (100) and a method (200), respectively, for automatic labeling of activity on the ECG data. The system (100) comprises an acquisition unit (101) for acquiring one or more of the physiological input relating to the ECG data. The physiological input includes but not limited to ECG signal, respiration data pertaining to the respiration of the subject, accelerometer data pertaining to sensing and measurement made by the accelerometer, health condition of the subject, SpO2 data etc.

A single lead ECG signal is obtained from the subject (201) by the acquisition unit (101). The ECG signal may be obtained using a wearable medical device comprising of sensor configured to measure one or more physiological parameters. The acquisition unit (101) includes but not limited to wearable medical devices.

The ECG signal is conditioned by conditioning unit of the processing unit (102). The conditioning of the ECG signal may be done by applying adaptive band pass filter (202), to eliminate the noise, baseline wander and interferences like power line interference. Adaptive band pass filter in the frequency range of 0.04 Hz to 150 Hz may be used to extract relevant signal from the ECG signal. The adaptive filter may consist of a single pole and a single zero as follows:

$$H_k(n, z) = \frac{b_k(n) + c_k(n)z^{-1}}{1 - a_k(n)z^{-1}}$$

Where ak, bk and ck are adaptive filter coefficients. $H_k$ is the transfer function, 'n' is the time index and 'z' is the Z-transform variable.

Figure 3:
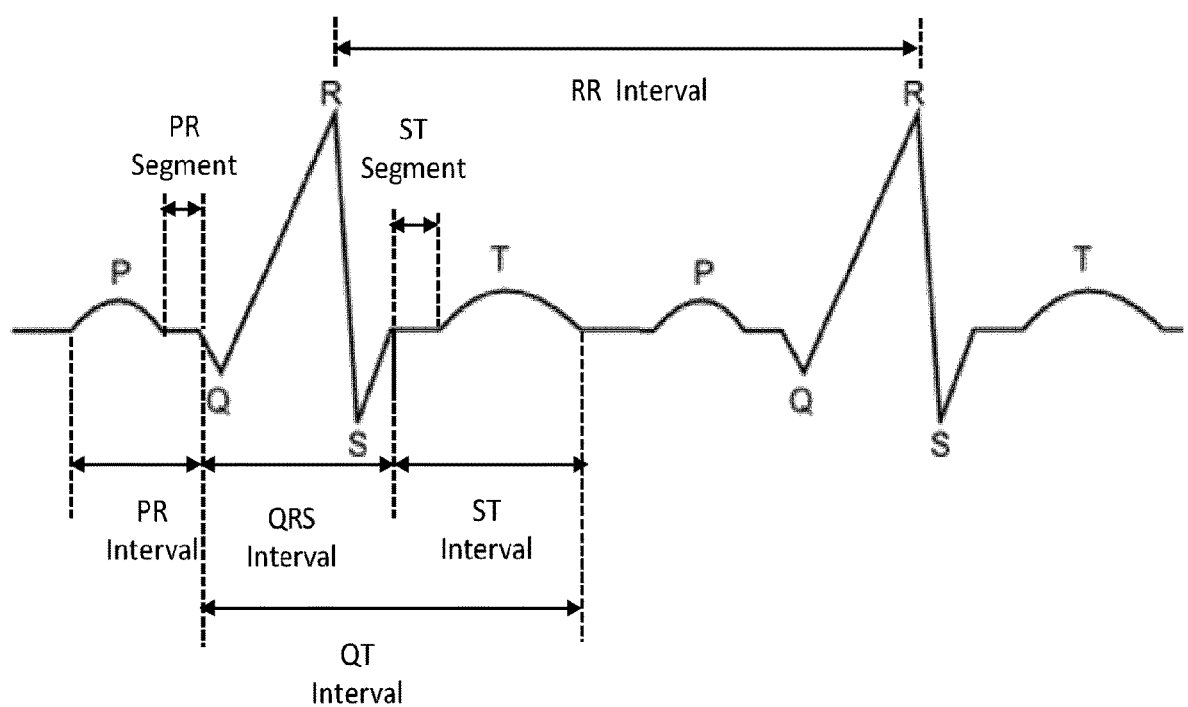
FIG. 3 shows the ECG data along with its fiducial points indicated therein.

As shown in FIG. 3, the typical ECG signal or data contains R-R peak variation when the subject exercises. However, this variation is not sufficient to clearly distinguish between different activities performed by the subject. The method (200) of the invention considers the variation in the fiducial (PQRS) points in the ECG signal based on the activity and also the morphological changes in the waveform.

The processing unit (102) is also provided for identifying the fiducial points on the ECG signal (203). Subsequent to applying the adaptive band pass filter, the fiducial points P, Q, R, S and T points are identified by the processing unit (102) in a given segment of the ECG signal. The R peak being more prominent in the ECG is initially identified using the frequency domain approach. The frequency domain transformed ECG signal is obtained as:

$$x_H(t) = \text{IFT}\{\text{FT}[x(t)]H(f)\}$$

Where, x(t) and $x_H(t)$ are the input and transformed ECG signals. FT and IFT represent Fourier transform and Inverse Fourier transform, respectively, and $$H(f) = \begin{cases} -j, & 0 < f < \pi \\ j, & -\pi < f < 0 \end{cases}$$

Where, H(F) is the Hilbert transform function.

A threshold may be employed on frequency domain transformed ECG signal to identify the peaks that are mapped back to the original signal for identification of R peaks. The first lowest minima on the left and right side of R peak forms the Q and S point, the time window of the search of Q and S with respect to R is empirically defined.

In order to determine P wave, a time window may be set prior to the beginning of QRS complex fiducial and QRS onset. The time window that approximately contains P wave is set heuristically and extended from QRS onset to the beginning of heartbeat. The beat begin fiducial point can be determined by searching of first isoelectric sample prior to the start of atrial deflection. For the detection of P waves, delineator computes the slope threshold, which is obtained by using the first derivative approach. The first derivative of the ECG, y(nT) at time instant T is calculated using the following time difference equation, where N being the length of the sample $$y(nT) = \frac{x(nT-(N-1)T) + x(nT-(N-2)T) + \ldots + x(nT))}{N}$$

The zero crossing of the differentiated signal maps to the P peak and succeeding the lowest crest on the differentiated signal maps to the P offset. Similar Fragment analysis approach is followed in determination of T peak by considering the segment in the ECG signal after S point (ST segment in FIG. 4).

Fragment analysis is performed (204) on the ECG signal after identifying the fiducial points, by the processing unit (102). R-R deviation, inversion of T peak, distance between fiducial points (QRS, P-QRS etc.) are computed. Other features that may be extracted from the fragment analysis are time interval from R peak to P off-set and P peak, time interval from R peak to S, and time interval from S to J point.

The processing unit (102) is also provided for fitting the ST and PQ segments of the ECG signal (205) based on the cubic spline fitting, to provide fitted segment of the ECG signal.

Figure 4:
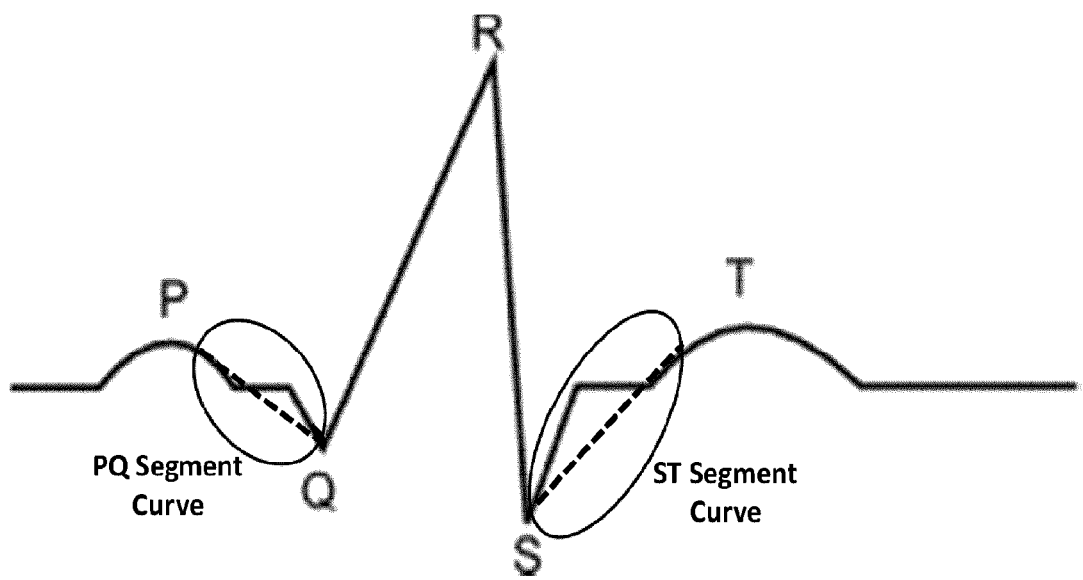
FIG. 4 illustrates the extraction of morphological structure of the ECG data relating to fiducial points.

Based on the analysis of the maximum frequency envelope, it may be observed that there exists a change in morphological structure in down sloping part of the ST and PQ segment, due to activity that been performed. In order to extract the change, the curve is cubic spline fit on these segments as shown in FIG. 4, and Karhunen Loeve Transform (KLT) is applied (206) to the fitted curve by the identification unit (103) so as to obtain principal component values. The KLT operation helps in revealing the internal structure of data in a way that best explains the variance in data. Further, the principal component values obtained after applying KLT act as the feature set for classification.

With Xi being the sample data vector fit on the ST or PQ segment, the covariance matrix of the data is computed as follows:

$$C = \frac{1}{n}\sum_{i=1}^{n} X_i X_i^T$$

Where $X_i$ is sample data vector of the fitted segment on the ECG, n is the number of samples, and C is the covariance matrix. Further, the Eigen value decomposition (207) is performed by the identification unit (103), on the covariance matrix C. The vectors associated with the corresponding Eigen value (principal values) are considered as the feature set. Similar feature vectors are extracted from the PQ segment.

The respiration rate acts as one of the primary indicators for differentiating the activities performed by the subject. If the heart rate and morphological changes are similar for two types of activities like sleeping and normal walking, respiration rate acts as a primary differentiating feature for correct labeling of these two types of activities. The respiration rate can be extracted from the ECG signal (208) based on well-known morphological changes in the fiducial points and the fragment analysis. However, the same information relating to respiration rate can also be extracted (208) from other sensor data such as accelerometer.

The identification unit (103) is also provided for classifying the feature set based on the classifier model and to map the feature set to its corresponding activity (209), thereby identifying the activity of the subject using ECG data and health condition of the subject.

The feature sets are fed to supervised Support Vector Machine (SVM) classifier. Here, the feature vectors are nonlinearly mapped to a higher dimension feature space and a linear separation surface is created to separate the training data by minimizing the margin between the vectors of the two classes. The training ends with the definition of a decision surface that divides the space into two subspaces. A good separation is achieved by the decision surface that has the largest distance to the nearest training data point of any class, wherein each subspace corresponds to one class of the training data.

Once the training is completed, the test data are mapped to the feature space. A class is then assigned to those data depending on corresponding subspace they are mapped to. The features in input space are transformed to a higher dimensional space. These features are then used for calculating a maximum margin hyperplane iteratively that provides best performance.

The aim of this classifier is to construct a decision function $f: R^N \rightarrow \{\pm 1\}$ using the given N-dimensional training data. Assuming a dataset represented by $$(x_1,y_1),(x_1,y_1),\ldots,(x_l,y_l) \in R^N\{\pm 1\}$$

where $x_1$ and $y_1$ represent feature vectors and class labels, respectively.

The hyperplane in multidimensional space is defined by linear discriminant functions given by $$g(x) = W^T x + \omega_0$$

where 'x' is the feature vector, W is the weight vector orthogonal to decision hyperplane and $\omega_0$ is the threshold. The weights and threshold parameters are optimised for each type of activities during model training phase.

Figure 5:
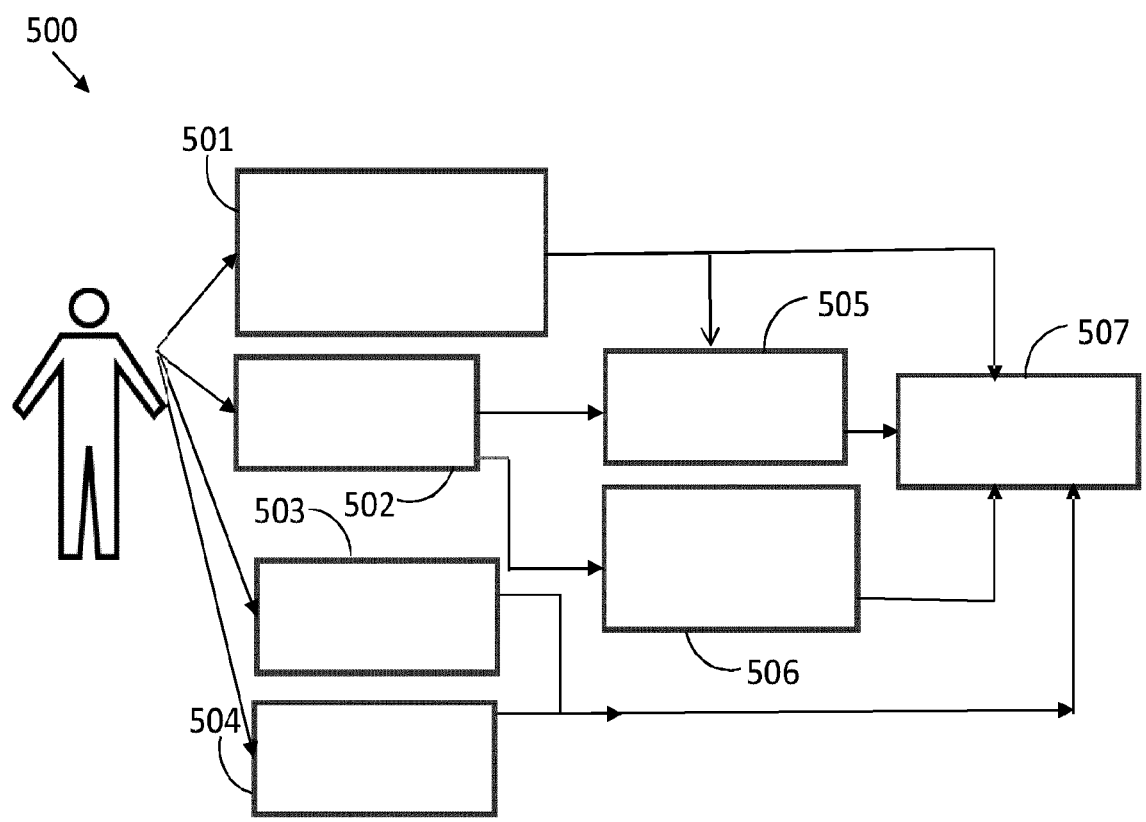
FIG. 5 illustrates the generation of classifier model.

As shown in FIG. 5 a classifier model is generated (500) based on certain parameter and/or physiological input for accurately predicting the activity type. Those parameters and/or physiological inputs include but not limited to information on activity captured by manual labeling and also along with accelerometer, health condition of the subject, SpO2 information, respiration rate, ECG data etc. In one embodiment, the classifier model (507) is trained or created (500) as shown in FIG. 5 based on the accelerometer data (501), ECG data (502), Health condition of the subject (503), SpO2 information (504), Respiration data (505), Fragment analysis of the ECG (506). The respiration data (505) may be obtained from the accelerometer data (501) and/or from the ECG data (502). Also, the fragment analysis of the ECG (506) is based on the ECG data (502) as described herein before.

In some subjects with Chronic Obstructive Pulmonary Disease (COPD), the subject will exhaust even for mild exertion, say in case of normal walking. For such subjects, even normal walking would increase their heart rate and respiratory rate, though they are performing a normal walk. Hence to differentiate correctly the status of the activity, the present health condition of the subject needs to be captured. The health condition of the subject may be captured by means of a questionnaire which will be part of the ECG recording. This information may be used in generating classifier model, contributing towards predicting the activity of the subject more accurately, which would otherwise be different from a healthy subject. The classifier model (507)

so generated has information pertaining to different activities and provides a basis for mapping different activities in correspondence with the ECG data.

The activity pertaining to the ECG data after being identified is labelled on the ECG data by marking the said activity on the ECG data automatically. The automatic labeling of the activity on the ECG data help to make informed decision in the diagnosis of the subject, based on the activity, health condition and exertion level of the subject. The time taken for diagnosis may also be reduced to a greater extent. The ECG data with the label relating to the activity may further be stored or uploaded accordingly. Uploading it into cloud also becomes possible and can be used more extensively as the case may be. This also provides better feedback and improved preventive care to the subject.

Only certain features of the invention have been specifically illustrated and described herein, and many modifications and changes will occur to those skilled in the art. The invention is not restricted by the preferred embodiment described herein in the description. It is to be noted that the invention is explained by way of exemplary embodiment and is neither exhaustive nor limiting. Certain aspects of the invention that not been elaborated herein in the description are well understood by one skilled in the art. Also, the terms relating to singular form used herein in the description also include its plurality and vice versa, wherever applicable. Any relevant modification or variation, which is not described specifically in the specification are in fact to be construed of being well within the scope of the invention. The appended claims are intended to cover all such modifications and changes which fall within the spirit of the invention.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. A method for automatic labeling of a plurality of activities of a subject using electrocardiography (ECG) data, the method comprising:
sensing, with a wearable medical device, an ECG signal having a plurality of segments, the plurality of segments including both a ST segment and a PQ segment;
conditioning, with an adaptive band pass filter, the sensed ECG signal;
subsequent to the conditioning with the adaptive band pass filter, identifying, with a processor, a plurality of fiducial points in the plurality of segments of the sensed ECG signal;
performing, with the processor, after identifying the plurality of fiducial points, fragment analysis on the segments of the sensed ECG signal, wherein the fragment analysis includes extraction of feature vectors from both the ST segment and the PQ segment;
generating a trained classifier model based on the fragment analysis of the sensed ECG signal;
mapping, with the trained classifier model, the plurality of activities based upon the sensed ECG signal;
obtaining, with the processor, a respiration rate based upon both the plurality of fiducial points and the fragment analysis;
differentiating, with the processor, based upon the respiration rate, the plurality of activities performed by the subject;
identifying, with the processor, a particular activity of the plurality of activities based upon variation in the plurality of fiducial points in the sensed ECG signal, the differentiating, and morphological changes in the ECG signal; and
storing, with the processor after identifying the particular activity, the sensed ECG signal with a label corresponding to the identified activity.

2. The method as claimed in claim 1, further comprising:
fitting the ST segment and the PQ segment of the sensed ECG signal based on cubic spline fitting to provide a fitted segment of the ECG signal.

3. The method as claimed in claim 2, further comprising:
applying a Karhunen Loeve Transform (KLT) on the fitted segment of the sensed ECG signal to obtain principal component values.

4. The method as claimed in claim 3, further comprising:
computing eigen values of the principal component values to obtain a feature set.

5. The method as claimed in claim 4, further comprising:
classifying the feature set based on the trained classifier model to map the feature set to a corresponding activity of the plurality of activities.

6. The method as claimed in claim 1, wherein the trained classifier model provides a basis for mapping different activities of the plurality of activities in correspondence with the sensed ECG signal.

7. The method as claimed in claim 6, further comprising:
marking the identified activity on the sensed ECG signal automatically, wherein the marking step corresponds to the stored label.

8. A system for automatic labeling of a plurality of activities of a subject using ECG data, the system comprising:
a wearable medical device configured to sense an ECG signal having a plurality of segments, the plurality of segments including both a ST segment and a PQ segment;
an adaptive band pass filter configured to condition the sensed ECG signal;
a processor configured to
identify, subsequent to the conditioning with the adaptive band pass filter, a plurality of fiducial points in the plurality of segments of the sensed ECG signal;
perform fragment analysis, after identifying the plurality of fiducial points, on the segments of the sensed ECG signal, wherein the fragment analysis includes extraction of feature vectors from both the ST segment and the PQ segment;
generate a trained classifier model based on the fragment analysis of the sensed ECG signal;
map, with the trained classifier model, the plurality of activities based upon the sensed ECG signal;
obtain a respiration rate based upon both the fiducial points and the fragment analysis;
differentiate based upon the respiration rate, the plurality of activities performed by the subject;
identify a particular activity of the plurality of activities based upon variation in the plurality of fiducial points in the sensed ECG signal, the differentiating, and morphological changes in the sensed ECG signal; and store, after identifying the particular activity, the sensed ECG signal with a label corresponding to the identified activity.

9. The system as claimed in claim 8, wherein the processor is further configured to fit the ST segment and the PQ segment of the sensed ECG signal based on cubic spline fitting to provide a fitted segment of the sensed ECG signal.

\* \* \* \* \*